(12) United States Patent
Hanson et al.

(10) Patent No.: US 8,551,128 B2
(45) Date of Patent: Oct. 8, 2013

(54) ROTATIONAL ATHERECTOMY DEVICE WITH PRE-CURVED DRIVE SHAFT

(75) Inventors: Scott M. Hanson, Minneapolis, MN (US); Walter Dobrovolny, St. Paul, MN (US); Jeffrey R. Stone, Chaska, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 388 days.

(21) Appl. No.: 11/951,870

(22) Filed: Dec. 6, 2007

(65) Prior Publication Data

US 2009/0149877 A1     Jun. 11, 2009

(51) Int. Cl.
*A61B 17/22* (2006.01)
(52) U.S. Cl.
USPC ........................................ 606/159
(58) Field of Classification Search
USPC ........... 606/108, 159, 167, 170, 171; 604/22, 604/508, 95.04, 93.01
See application file for complete search history.

(56) References Cited

U.S. PATENT DOCUMENTS

| | | | |
|---|---|---|---|
| 4,990,134 A | 2/1991 | Auth | |
| 5,217,474 A * | 6/1993 | Zacca et al. | 606/159 |
| 5,308,354 A * | 5/1994 | Zacca et al. | 606/159 |
| 5,312,427 A * | 5/1994 | Shturman | 606/159 |
| 5,314,438 A * | 5/1994 | Shturman | 606/159 |
| 5,356,418 A * | 10/1994 | Shturman | 606/159 |
| 5,360,432 A | 11/1994 | Shturman | |
| 5,554,163 A * | 9/1996 | Shturman | 606/159 |
| 5,584,843 A | 12/1996 | Wulfman et al. | |
| 5,681,336 A | 10/1997 | Clement et al. | |
| 5,766,192 A * | 6/1998 | Zacca | 606/159 |
| 5,843,103 A | 12/1998 | Wulfman | |
| 5,853,408 A | 12/1998 | Muni | |
| 5,897,566 A * | 4/1999 | Shturman et al. | 606/159 |
| 6,129,750 A * | 10/2000 | Tockman et al. | 607/125 |
| 6,132,444 A | 10/2000 | Shturman et al. | |
| 6,146,395 A | 11/2000 | Kanz et al. | |
| 6,156,046 A | 12/2000 | Passafaro et al. | |
| 6,156,048 A * | 12/2000 | Wulfman et al. | 606/159 |
| 6,416,523 B1 | 7/2002 | Lafontaine | |
| 6,494,890 B1 * | 12/2002 | Shturman et al. | 606/159 |

(Continued)

FOREIGN PATENT DOCUMENTS

| | | |
|---|---|---|
| EP | 1 350 473 | 8/2003 |
| JP | 2002-506668 | 3/2002 |
| WO | WO94/08519 | 4/1994 |
| WO | WO01/54754 | 8/2001 |

*Primary Examiner* — Ryan Severson
*Assistant Examiner* — David Eastwood
(74) *Attorney, Agent, or Firm* — Winthrop & Weinstine, P.A.

(57) ABSTRACT

The invention provides a rotational atherectomy system, device and method comprising a flexible, elongated, rotatable drive shaft with an abrasive section within a pre-curved section of the drive shaft. The device may further comprise a concentric or eccentric enlarged diameter section that is at least partially covered with abrasive material to comprise the abrasive section. The abrasive section may further comprise an abrasive crown or burr mounted to the drive shaft. The pre-curved drive shaft allows smaller diameter and/or massive abrasive regions to be used while sweeping larger diameters during high-speed rotation. The pre-curved region is substantially straightened for insertion into vasculature and placement adjacent stenosis by insertion of the guide wire. Removal of guide wire proximally from the pre-curved region allows the drive shaft to return to its pre-curved form for ablation. Reinsertion of the guide wire beyond the pre-curved region straightens the drive shaft for ease of removal.

34 Claims, 8 Drawing Sheets

(56) References Cited

U.S. PATENT DOCUMENTS

| | | |
|---|---|---|
| 6,596,005 B1 | 7/2003 | Kanz et al. |
| 6,638,288 B1 * | 10/2003 | Shturman et al. ............ 606/159 |
| 6,663,613 B1 * | 12/2003 | Evans et al. .................. 604/523 |
| 7,037,316 B2 * | 5/2006 | McGuckin et al. ........... 606/159 |
| 2003/0125756 A1 * | 7/2003 | Shturman et al. ............ 606/159 |
| 2005/0149083 A1 * | 7/2005 | Prudnikov et al. ........... 606/159 |

* cited by examiner

ROTATIONAL ATHERECTOMY DEVICE WITH PRE-CURVED DRIVE SHAFT

BACKGROUND OF THE INVENTION

1. Field of the Invention

The invention relates to devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a concentrically shaped ellipsoidal burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently, since the burr is of a fixed resting diameter, more than one size burr must be utilized to open an artery to the desired diameter. No other variables are disclosed by the Auth device that would allow sweeping a variable diameter, or a diameter larger than the burr's resting diameter, during high-speed rotation.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., rotational speeds within the range of about 20,000-200,000 rpm. Essentially, the center of mass offset from the rotational axis of the drive shaft would result in development of significant and undesirable centrifugal force, exerting too much pressure on the wall of the artery and creating too much heat and excessively large particles. As with Auth, the burr size is fixed and may require using more than one size burr to open the subject lumen to the desired diameter.

U.S. Pat. No. 6,132,444 (Shturman) and U.S. Pat. No. 6,494,890 (Shturman) both commonly assigned, disclose, inter alia, an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The orbital rotational motion is primarily due to the offset of the center of mass of the enlarged eccentric section from the drive shaft's rotational axis. Since the enlarged eccentric section may comprise drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. The disclosure of U.S. Pat. Nos. 6,132,444 and 6,494,890 are each hereby incorporated by reference in their entirety.

Commonly assigned U.S. application Ser. No. 11/876,891 to Prudnikov entitled Rotational Atherectomy Device With Counterweights, the disclosure of which is hereby incorporated in its entirety, describes the use of counterweights to stimulate, or dampen, orbital motion of an abrasive section. The techniques, methods and apparatus described therein may be used to generate a rotational diameter of the abrasive section that is greater than the resting diameter of the abrasive section.

Other techniques and devices have been proposed to generate a rotational sweeping diameter that is greater than the resting diameter of the abrasive section. Generally, these include a pre-bent guide wire that will, when placed within the lumen of a rotational drive shaft, create a bend in the drive shaft at the abrasive region. When the guide wire is removed, the drive shaft returns to its normal uncurved and substantially linear shape. Such an arrangement will, when the pre-bent guide wire is in place, create a sweeping diameter for the abrasive region of the drive shaft that is greater than its resting diameter. Examples of such pre-bent guide wire proposals include U.S. Pat. Nos. 5,312,427, 5,356,418, 5,554,163 all to Shturman and commonly assigned with the present application. Other examples include U.S. Pat. No. 5,548,843 to Wulfman and U.S. Pat. No. 6,156,046 to Passafaro.

The pre-curved guide wire designs each require the guide wire to be in place within the lumen of the drive shaft to create the desired bending of the drive shaft and abrasive region which may hamper flexibility of the drive shaft during high-speed rotation. Further, the pre-curved guide wire approach may find difficulty in traversing the often tortuous vasculature enroute to the stenosis of interest.

Thus, it would be highly advantageous to provide an atherectomy system, device and method that is substantially linear upon entry into the patient's vasculature but at the same time allows for expansion of the sweeping diameter of the drive shaft's abrasive region based, at least in part, upon pre-bending of the drive shaft itself, not the guide wire as previously proposed.

The present invention addresses, inter alia, these needs.

BRIEF SUMMARY OF THE INVENTION

The invention provides a rotational atherectomy system, device and method comprising a flexible, elongated, rotatable drive shaft with an abrasive section disposed within a pre-curved section of the drive shaft. The device may further comprise a concentric or eccentric enlarged diameter section that is at least partially covered with abrasive material to comprise the abrasive section. The abrasive section may further comprise an abrasive crown or burr mounted to the drive shaft. The pre-curved drive shaft allows smaller diameter and/or massive abrasive regions to be used while sweeping larger diameters during high-speed rotation. The pre-curved region is substantially straightened for insertion into vasculature and placement adjacent stenosis by insertion of the guide wire. Removal of guide wire proximally from the pre-curved region allows the drive shaft to return to its pre-curved form for ablation. Reinsertion of the guide wire beyond the pre-curved region straightens the drive shaft for ease of removal.

An object of the invention is to provide a high-speed rotational atherectomy device having an abrasive section with a high-speed rotational diameter that is greater than its resting diameter.

Another object of the invention is to provide a high-speed rotational atherectomy device having an abrasive section on a pre-curved region of the drive shaft.

Another object of the invention is to provide a high-speed rotational atherectomy device with a pre-curved region of the drive shaft and comprising an enlarged section of the drive shaft within the pre-curved region.

Another object of the invention is to provide a high-speed rotational atherectomy device with a pre-curved region of the drive shaft and comprising a concentric enlarged abrasive section of the drive shaft within the pre-curved region.

Another object of the invention is to provide a high-speed rotational atherectomy device with a pre-curved region of the drive shaft and comprising an eccentric enlarged abrasive section of the drive shaft within the pre-curved region.

Another object of the invention is to provide a high-speed rotational atherectomy device with a pre-curved region of the drive shaft and comprising an eccentric at least partially solid crown attached to the drive shaft within the pre-curved region.

Another object of the invention is to provide a high-speed rotational atherectomy device with a pre-curved region of the drive shaft and comprising an abrasive burr attached to the drive shaft within the pre-curved region.

Another object of the invention is to provide a high-speed rotational atherectomy device with a pre-curved region of the drive shaft and comprising a concentric abrasive burr attached to the drive shaft within the pre-curved region.

Another object of the invention is to provide a high-speed rotational atherectomy device with a pre-curved region of the drive shaft and comprising an eccentric abrasive burr attached to the drive shaft within the pre-curved region.

Another object of the invention is to provide a high-speed rotational atherectomy device with a pre-curved region of the drive shaft and comprising an abrasive annular ring attached to the drive shaft within the pre-curved region.

Another object of the invention is to provide a high-speed rotational atherectomy device with a pre-curved region of the drive shaft having a curvilinear profile that is dynamically adaptable.

Another object of the invention is to provide a system and methods to achieve, inter alia, the above objectives.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
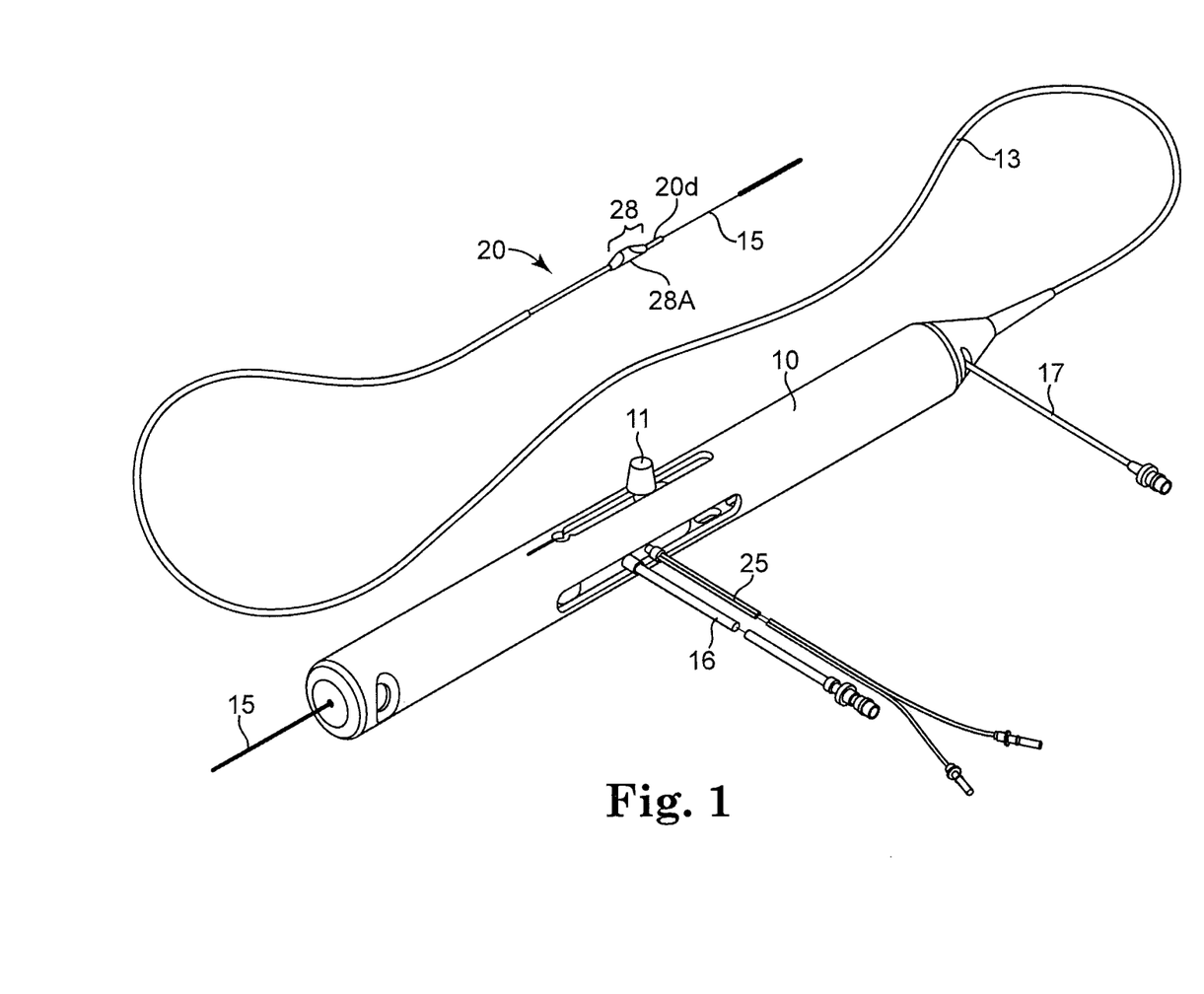
FIG. 1 is a perspective view of one embodiment of the present invention.

FIG. 1 illustrates one embodiment of a rotational atherectomy system and device of the present invention. The system includes a handle portion 10, an elongated, flexible drive shaft 20 having an abrasive section 28 comprising an abrasive section 28, illustrated without limitation as an eccentric crown 28A, which is attached to drive shaft 20, and an elongated catheter 13 extending distally from the handle portion 10. The drive shaft 20 is constructed from helically coiled wire and, as illustrated comprise an eccentric crown 28A attached thereto. The catheter 13 has a lumen in which most of the length of the drive shaft 20 is disposed, including in some embodiments the abrasive section 28, and a short section distal 20*d* to the abrasive section 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13. In certain embodiments warming biocompatible fluid may be introduced into the catheter 13. Generally, abrasive section 28A, e.g., eccentric crown 28A, comprises an abrasive coating at least partially thereon to facilitate tissue removal. Alternatively, the surface of abrasive section 28, e.g., eccentric crown 28A, may be at least partially roughened and/or etched to facilitate tissue removal.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25 may also be provided for monitoring the speed of rotation of the turbine and drive shaft 20 (details regarding such handles and associated instrumentation are well known in the industry. The handle 10 also desirably includes a control knob 11 for advancing and retracting the turbine and drive shaft 20 with respect to the catheter 13 and the body of the handle 10.

As illustrated, drive shaft 20 is substantially linear or straight, with guide wire 15 disposed through the drive shaft inner lumen, with guide wire 15 extending through and beyond the abrasive section 28.

Figure 2:
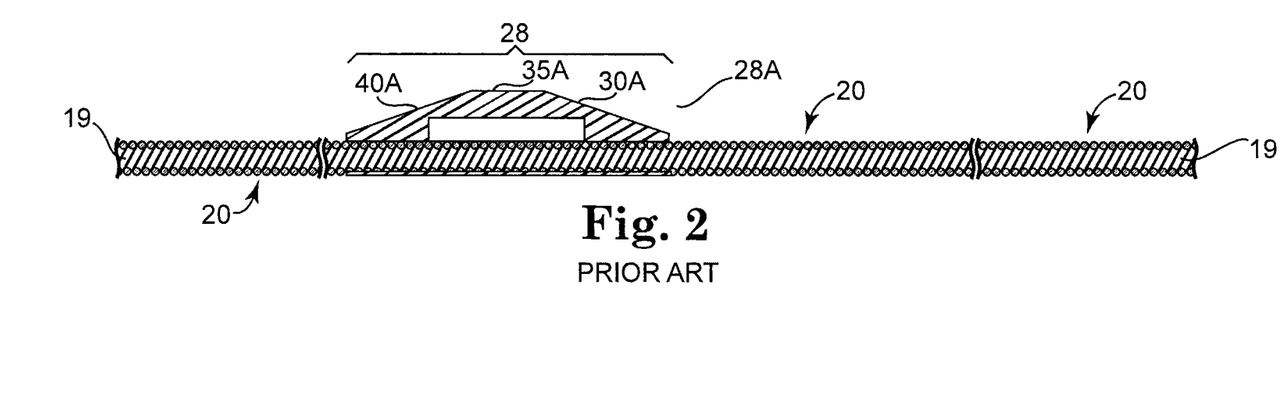
FIG. 2 is a cutaway side view of one embodiment of a prior art device.
Figure 3:
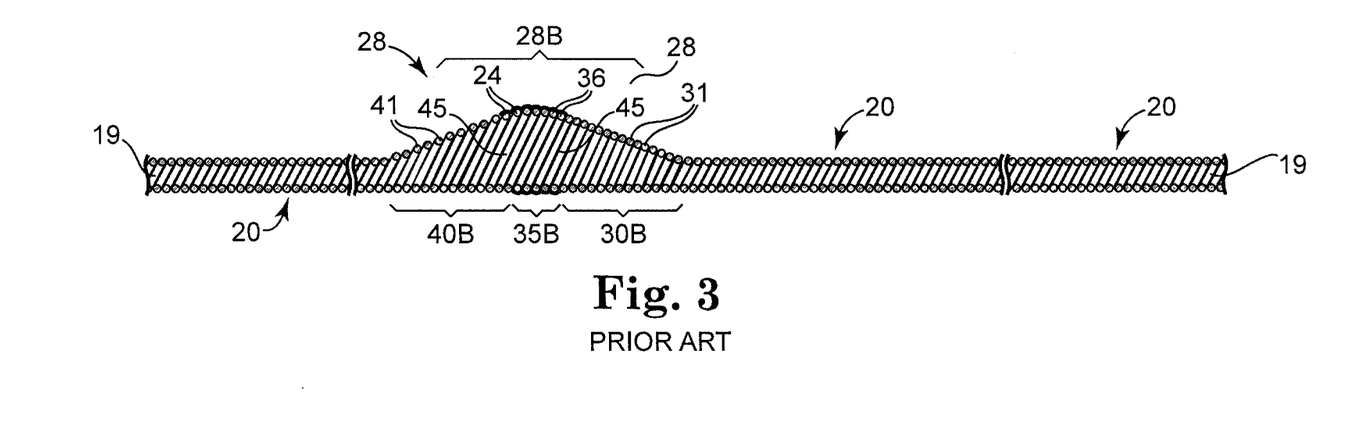
FIG. 3 is a cutaway side view of one embodiment a prior art device.

With reference now to FIGS. 2 and 3, two embodiments of prior art abrasive sections 28 are illustrated. FIG. 2 provides a cross-sectional view of a rotational drive shaft 20 with lumen 19 therethrough. The device is illustrated as substantially linear and without a guide wire disposed within drive shaft lumen 19. Further, an eccentric solid crown 28A is illustrated as comprising the abrasive section 28. Eccentric solid crown 28A comprises comprises proximal 30A, intermediate 35A and distal 40A portions. An abrasive (not shown) may be coated upon one or more of the proximal 30A, intermediate 35A and distal 40A portions as is well known to those skilled in the art. By way of example, the abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the wire turns of the drive shaft 20 by a suitable binder 26—such attachment may be achieved using well known techniques, such as conventional electroplating or fusion technologies (see, e.g., U.S. Pat. No. 4,018,576). Alternately the external tissue removing surface may be simply a section of the wire turns which has been roughened to provide a suitable abrasive surface. In yet another variation, the external surface may be etched or cut (e.g., with a laser) to provide small but sharp cutting surfaces. Other similar techniques may also be utilized to provide a suitable tissue removing surface.

FIG. 3 illustrates another prior art embodiment, wherein the drive shaft 20 with abrasive section 28 comprising an eccentric enlarged section 28B of drive shaft 20 with lumen 19 therethrough for receiving guide wire (not shown). The drive shaft 20 is, as with the FIG. 2 device, substantially linear without guide wire disposed within lumen 19.

Drive shaft 20 is comprised of one or more helically wound wires 18 which define a guide wire lumen 19 and a hollow cavity 45 within the enlarged diameter section 28B. Enlarged diameter section 28B comprises proximal 30B, intermediate 35B and distal 40B portions. Wire turns 31 of the proximal portion 30 of the eccentric enlarged diameter section 28B preferably have diameters that progressively increase distally at a generally constant rate, thereby forming generally the shape of a cone. Wire turns 41 of the distal portion 40 preferably have diameters that progressively decrease distally at a generally constant rate, thereby forming generally the shape of a cone. Wire turns 36 of the intermediate portion 35B are provided with gradually changing diameters to provide a generally convex outer surface which is shaped to provide a smooth transition between the proximal and distal conical portions of the enlarged diameter section 28B of the drive shaft 20.

At least part of the abrasive section 28, illustrated as eccentric enlarged diameter section 28B (preferably the intermediate portion 35) may comprise a coating 36 of an abrasive material 24 to define a tissue removing segment of the drive shaft 20. Abrasive section 28, comprising enlarged diameter section 28B, may have the tissue removing segment formed by methods and materials and techniques described above in connection with FIGS. 1 and 2.

Figure 4:
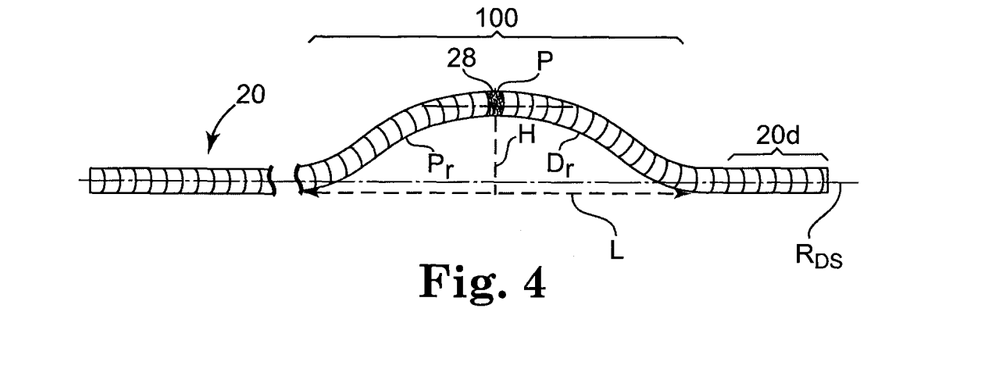
FIG. 4 is a side view of one embodiment of the present invention.
Figure 5:
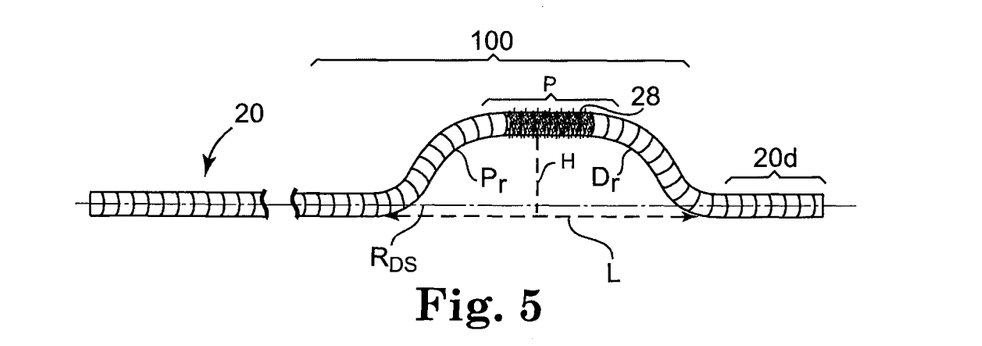
FIG. 5 is a side view of one embodiment of the present invention.

Turning now to FIGS. 4 and 5, two alternate embodiments of a drive shaft 20 of the present invention are illustrated. Each embodiment comprises a pre-curved section 100 having a curvilinear profile and which further comprises an abrasive section 28 formed and/or operatively disposed on the drive shaft 20 at least partly at the peak P of the pre-curved section 100. Preferably, pre-curved section 100 is formed on the drive shaft 20 proximal to distal portion of drive shaft $20_d$. Abrasive section 28 is illustrated as having abrasive disposed directly on the drive shaft 20 without any further manipulation to the profile of drive shaft 20, i.e., enlarging a section of the drive shaft as described above.

As shown in FIG. 4, peak P of pre-curved section 100 may be a substantially discreet point or, as in FIG. 5, a series of substantially linear points as the peak P may comprise a substantially linear profile. Abrasive section 28 may be formed and/or operatively disposed at least partly at peak P in either embodiment. Moreover, each pre-curved section 100 further comprises a height H and a length L as shown in the Figures.

In certain embodiments, the curvilinear profile, defined, e.g., by height H and the length L and radius/radii of the pre-curved section 100 may be adapted, and in some embodiments dynamically adaptable as will be further described infra, to the changing geometries of a passageway within a stenosis or body lumen. For example, the height H to length L ratio may preferably be in the range from 0.1:1 to 5:1, though the skilled artisan will recognize that height H to length L ratios greater than 5:1 will certainly have application; each such ratio is within the scope of the present invention.

Moreover, in certain embodiments as will be further described herein, the height H and the length L of the pre-curved section 100 may be changed by the operator in certain embodiments of the present invention as the stenosis is progressively abraded away by the present invention. Specifically, the height H may be increased (or decreased) and the length L may be increased (or decreased) depending on the particular needs and the prevailing environment at the time, i.e., the size of the passageway through the stenosis.

Pre-curved section 100 further comprises at least one radiused section, preferably two radiused sections, and may further comprise a substantially linear section as shown in FIG. 5 corresponding to peak P, wherein the peak P is substantially linear and substantially parallel with the sections of drive shaft 20 that are proximal and distal the pre-curved section 100. For example, a proximal radiused section $P_r$ and a distal radiused section $D_r$ may be provided with peak P therebetween. The radiused section(s) may vary in curvature and may, or may not, comprise substantially equivalent curvatures. Orbital motion may be induced by radiused sections that do not have equivalent curvature. Those skilled in the art will recognize the varying radius and/or radii and curvature thereof, height H, length L and profile form of peak P comprise a plurality of parameters that may form a wide variety of combinations; each such combination is within the scope of the present invention.

It can now be readily seen that the illustrated embodiments in FIGS. 4 and 5 comprise the abrasive section 28, disposed generally at peak P, as being transversely offset from the rotational axis of the non-curved and substantially linear portions of drive shaft $R_{DS}$, such transverse offset being generally defined by height H of precurved section 100.

Figure 5A:
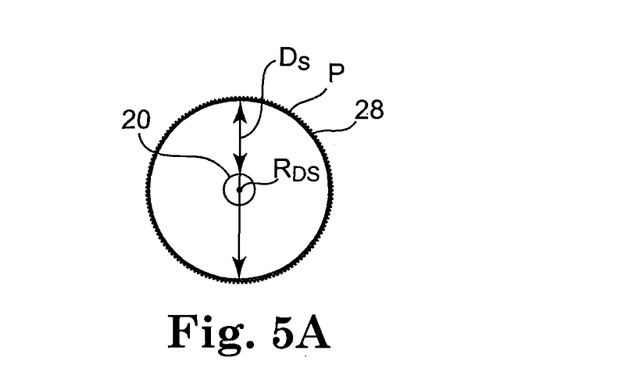
FIG. 5A is a cutaway end view of one embodiment of the present invention.

FIG. 5A illustrates an end on cutaway view of one embodiment of the present invention during high-speed rotation, with the cutaway achieved within abrasive section 28 and at or within peak P. Thus, drive shaft 20 is shown with rotational drive shaft axis denoted as $R_{DS}$. The rotational path of peak P of pre-curved section 100 as illustrated in FIGS. 4 and 5 is shown with abrasive section 28 disposed thereon. The swept diameter $D_S$ achieved as drive shaft 20 rotates illustrates the enlarged sweeping rotational path of the pre-curved section 100, specifically for peak P of pre-curved section 100 as compared with the rotational sweep of the non-curved portions of drive shaft 20 which is essentially limited to the resting diameter of drive shaft 20. As illustrated, peak P of pre-curved section 100 rotates concentrically about $R_{DS}$, though alternate embodiments may comprise an eccentric rotation about $R_{DS}$ to induce orbital motion of peak P and abrasive section 28.

Moreover, those skilled in the art will recognize that providing an abrasive section 28 with an eccentric crown or burr or enlarged drive section of the drive shaft as described herein will tend to place additional force on the peak P section of pre-curved section 100 during high-speed rotation which will, in turn, tend to increase the distance of the rotational path of peak P, i.e., enlarging the swept diameter diameter $D_S$. Such an arrangement may further induce orbital motion.

As discussed herein, the abrasive section 28 formed and/or operatively disposed at least partly at peak P may comprise many different forms, each of which are within the scope of the present invention. For example, and without limitation, abrasive section 28 may simply be an abrasive formed on or coated onto the cylindrically-shaped drive shaft 20 as illustrated in FIGS. 4 and 5, wherein abrasive material is coated thereon, specifically diamond dust or the equivalent, or formed thereon by etching or the equivalent, each such technique being well known in the art.

Alternatively the abrasive section may comprise an eccentric enlarged section of the drive shaft coated at least partially with abrasive, as described in detail in commonly assigned U.S. Pat. No. 6,494,890, the disclosure of which is incorporated herein in its entirety insofar as it describes an abrasive section comprising an eccentric enlarged section of the drive shaft 20 that is coated with an abrasive. Still more alternatively the abrasive section may comprise a concentric enlarged section of the drive shaft coated at least partially with abrasive, as described in detail in commonly assigned U.S. Pat. No. 5,314,438, the disclosure of which is incorporated herein in its entirety insofar as it describes an abrasive section comprising a concentric enlarged section of the drive shaft 20 that is coated with an abrasive.

Still more alternatively, the abrasive section may comprise a concentric burr or an eccentric burr, or a concentric, or an eccentric crown as described in commonly assigned U.S. patent application Ser. No. 11/761,128 the disclosure of which is incorporated herein in its entirety insofar as it describes an eccentric crown attached to the drive shaft 20 and at least partially coated with abrasive, or an annular abrasive ring as described in commonly assigned U.S. patent application Ser. No. 10/272,164 the disclosure of which is incorporated herein in its entirety insofar as it describes an abrasive section comprising an annular ring or sleeve coated with abrasive that is slid over and attached to the drive shaft 20, each of which may be attached to the drive shaft 20 at the peak of the pre-curved section, whether the drive shaft 20 comprises a cylindrical profile at the abrasive section as illustrated in FIGS. 4 and 5, or a concentric or eccentric enlarged diameter section as discussed above.

It should be understood that, as used herein, the word "eccentric" is defined herein to mean either a difference in location between the geometric center of the abrasive section 28, in its various alternate embodiments as described herein, and the rotational axis of the drive shaft, or to a difference in location between the center of mass of the eccentric abrasive section 28, in its various alternate embodiments as described herein, and the rotational axis of the drive shaft 20. These parameters at the proper rotational speeds, will enable the abrasive section 28 to open a stenosis to a diameter substantially greater than the nominal diameter of the abrasive section 28. Moreover, for an eccentric abrasive section 28 having a shape that is not a regular geometric shape, the concept of "geometric center" can be approximated by locating the midpoint of the longest chord which is drawn through the rotational axis of the drive shaft and connects two points on a perimeter of a transverse cross-section taken at a position where the perimeter of the eccentric enlarged diameter section has its maximum length. Moreover, those skilled in the art will recognize that eccentricity as defined may be designed into an abrasive section 28 having a substantially concentric profile, but with one aspect of the profile being more massive than the rest by, e.g., hollowing out a portion of one side of the abrasive section 28. Further, eccentric as used to describe the rotational diameter of abrasive section 28 of the present invention means that the rotational radii are not substantially equivalent around the circumference of the rotational path of abrasive section 28, thus an orbital pathway for the abrasive section 28 is developed.

Moreover, it should also be understood that concentric as used herein, is defined to mean an abrasive section 28 that comprises a center of mass that is on, i.e., collinear with, the axis of rotation of the drive shaft 20 and a profile that is substantially symmetrical. Moreover concentric as used in connection with the rotational diameter of abrasive section 28 of the present invention means that the rotational radii are substantially equivalent around the circumference of the rotational path of abrasive section 28.

The apparatus and system having been described, the method of formation of the pre-curved section 100 will now be discussed in detail.

The pre-curved section 100 may be fixedly formed or adapted by a variety of techniques, one of which comprises a unique heat setting method. Under this method, initially, the drive shaft 20 is wound using a coil winder as is well known in the art. Next, the entire length of wound drive shaft 20 receives a 200 degree C. heat set for one hour to relax and stabilize the coil dimensions. Treatments of this type are common in spring and coil manufacturing and are intended to pre-relax the wound drive shaft 20 coils. The skilled artisan will recognize additional variations of time and temperature for the pre-relaxation step, each such variation being within the scope of the present invention, thus the particular parameters provided are for illustration only and in no way limit the scope of the present invention.

Next, a mandrel shaped in the desired curved drive shaft form is inserted into the lumen 19 at the distal end of the straight (and pre-relaxed) drive shaft 20. Thus, the drive shaft 20 is forced to take on the shape of the mandrel. The mandrel may be formed of and/or comprise materials well known to those skilled in the art, including, inter alia, stainless steel.

After the mandrel is in place within the drive shaft lumen 19, a local heat treatment is performed on the curved portion of the drive shaft 20 is performed with the mandrel in place using well known techniques. Typical local heat treatment conditions for this step of the method may comprise exposing the curved section with mandrel therein to a heat of 555 degrees C. for 30 minutes, though these particular parameters in no way limit the scope of the invention. To the contrary, those skilled in the art will recognize additional variations of time and temperature for the local heat treatment step, each such variation being within the scope of the present invention. The local heat treatment provides much greater stress relief than the previous pre-relaxation heat treatment step and, in addition, provides the activation energy necessary to relieve even the lower energy dislocation sites within the section of the drive shaft 20 to be curved under the curving process. Dislocations in the drive shaft 20 filars are set such that they promote the bent shape even without aid from the mandrel.

After the local heat treatment is complete, the mandrel is removed and the curved shape is retained by the drive shaft 20 thus forming the pre-curved section 100 of the present invention. Thus, the described technique provides a pre-set and non-dynamically adaptable pre-curved section 100 of fixed height H and length L and adapted curvilinear profile. Alternate method steps may comprise electrolytic polishing of the pre-curved section 100, particularly the portion of the drive shaft 20 that was subjected to the local heat treatment, to remove any oxidation.

Other mechanisms and methods for forming the pre-curved section 100 of the present invention may comprise using shape memory alloy materials and are contemplated under the present invention. One example of a material that can be used for the pre-curved section is a shape memory alloy such as nickel-titanium (NiTi), commonly referred to as Nitinol. Nitinol exhibits superelastic properties and increased flexibility over conventional stainless steel which may ease the insertion of the guide wire 15 through the drive shaft lumen 19, including the pre-curved section 100 during placement of the abrasive section 28 proximate the target stenosis.

Examples of superelastic metal alloys, including Nitinol, which are usable to form certain embodiments of the pre-curved section 100 of the present invention are described in detail in U.S. Pat. No. 4,665,906. The disclosure of U.S. Pat. No. 4,665,906 is expressly incorporated herein by reference insofar as it describes the compositions, properties, chemistries, and behavior of specific metal alloys which are superelastic within the temperature range at which the pre-curved section 100 of the drive shaft 20 of the present invention operates, any and all of which superelastic metal alloys may be usable to form the pre-curved section 100 of the drive shaft 20.

Regardless of the method and/or materials used to achieve the pre-curved section 100 of the present invention, pre-curved section 100 is provided in its pre-curved configuration with curved profile as described above prior to insertion into patient's vasculature. The pre-curved section 100 is then mechanically deformed to a generally linear and/or straight configuration and profile by insertion of the substantially linear guide wire 15 through the drive shaft lumen 19. After the drive shaft 20 and guide wire 15 combination, inter alia, has been introduced into the target blood vessel for use according to the methods described herein, the guide wire 15 may be removed proximally and the pre-curved section 100 of the drive shaft 200 is thus allowed to return to its original pre-curved configuration and profile, at either its maximum height H and length L diameter, or other height H and length L if, for example a shape memory allow such as Nitinol is used for the pre-curved section 100.

Moreover, depending on the operation mode employed, as described below, dynamic adaptability of the curvilinear profile by manipulating, e.g., height H and length L, of pre-curved section 100 may be employed by, e.g., thermally inducing the pre-curved section 100 embodiment comprising a shape memory allow such as Nitinol, to cause it to return to its original configuration (either the maximum height H and length L, or varying lengths of H and L).

One example of dynamic adaptable control over the pre-curved section's 100 curvilinear profile, e.g., height H and length L parameters may be achieved by application of a controlled amount of thermal (or cooling) energy to the pre-curved section 100 which, in this embodiment, comprises a shape memory alloy such as Nitinol. In such an arrangement, the curvilinear profile of the pre-curved section may be made to be more flat, i.e., a smaller height H parameter by cooling the pre-curved section 100. Alternatively, the curvilinear profile may be made to have a greater height H by adding thermal energy to the pre-curved section 100.

Figure 7:
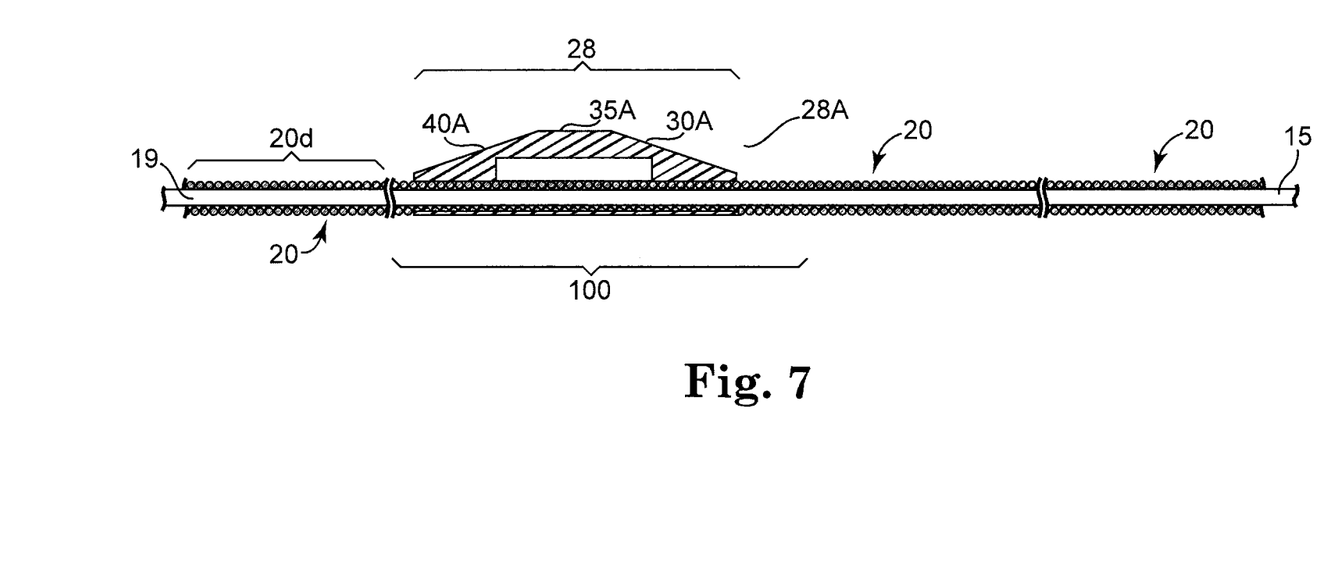
FIG. 7 is a cutaway side view of one embodiment of the present invention.
Figure 9:
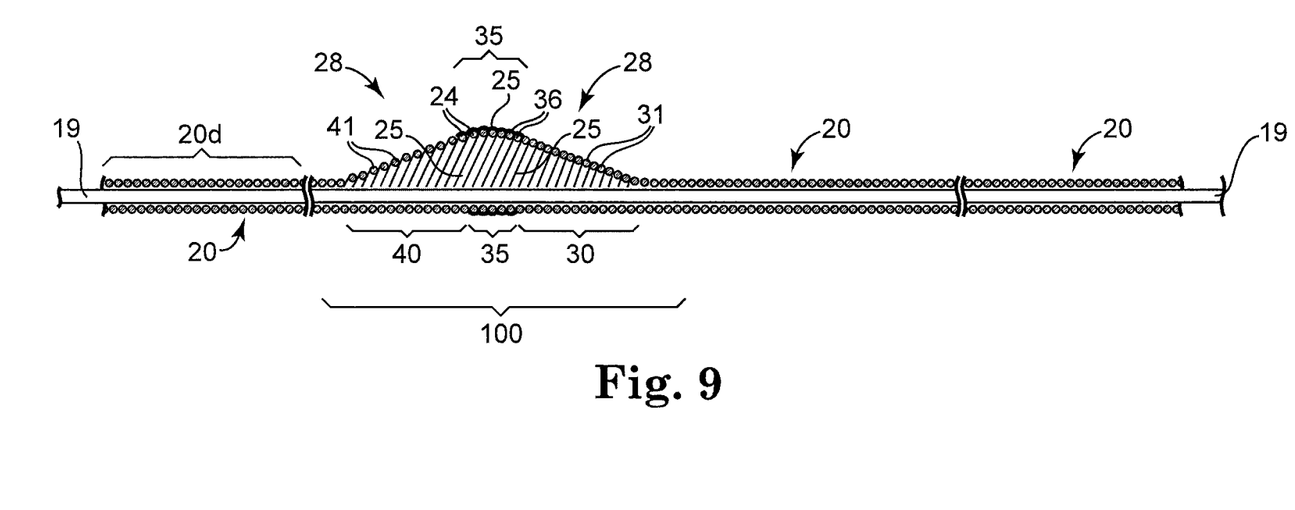
FIG. 9 is a cutaway side view of one embodiment of the present invention.

For example, and without limitation, heat may be applied to the pre-curved section 100 by bathing the pre-curved section 100 in a heated and/or heat-controlled physiologically compatible fluid (e.g., saline, Ringer's Solution, etc.) that is introduced via the lumen of guide catheter 13 as illustrated in FIGS. 1, 7 and 9, through which the drive shaft 20 is introduced. By controlling the temperature of the fluid introduced, either warming or cooling, the temperature of the pre-curved section 100 is similarly controlled such that when guide wire 15 is proximally withdrawn beyond the pre-curved section 100, the curvilinear profile is proportionally and controllingly affected. This allows further dynamic and adaptable control of the pre-curved section's 100 curvilinear profile, e.g., height H and length L, to a plurality of curvilinear profiles to match the vascular environment without requiring the operator to remove the device mid-procedure.

Alternatively, dynamic adaptable control over the shape memory alloy pre-curved section 100 height H and length L parameters to dynamically adapt the pre-curved section 100 to a variety of curvilinear profiles may be achieved by controlling the temperature of the pre-curved section 100 by passing current through the guide wire 15 from its proximal end and then removing the guide wire 15 proximally to allow the pre-curved section 100 to controllably achieve its pre-curved configuration and profile with height H and length L proportional to the heat generated in pre-curved section by the current applied as described. Alternatively, a cooling effect may be realized by using a Peltier device as is well known in the art. As those skilled in the art will recognize, the application of electrical current to the guide wire 15 may be accomplished by attaching one or two leads to the proximal end of the guide wire 15.

Figure 6:
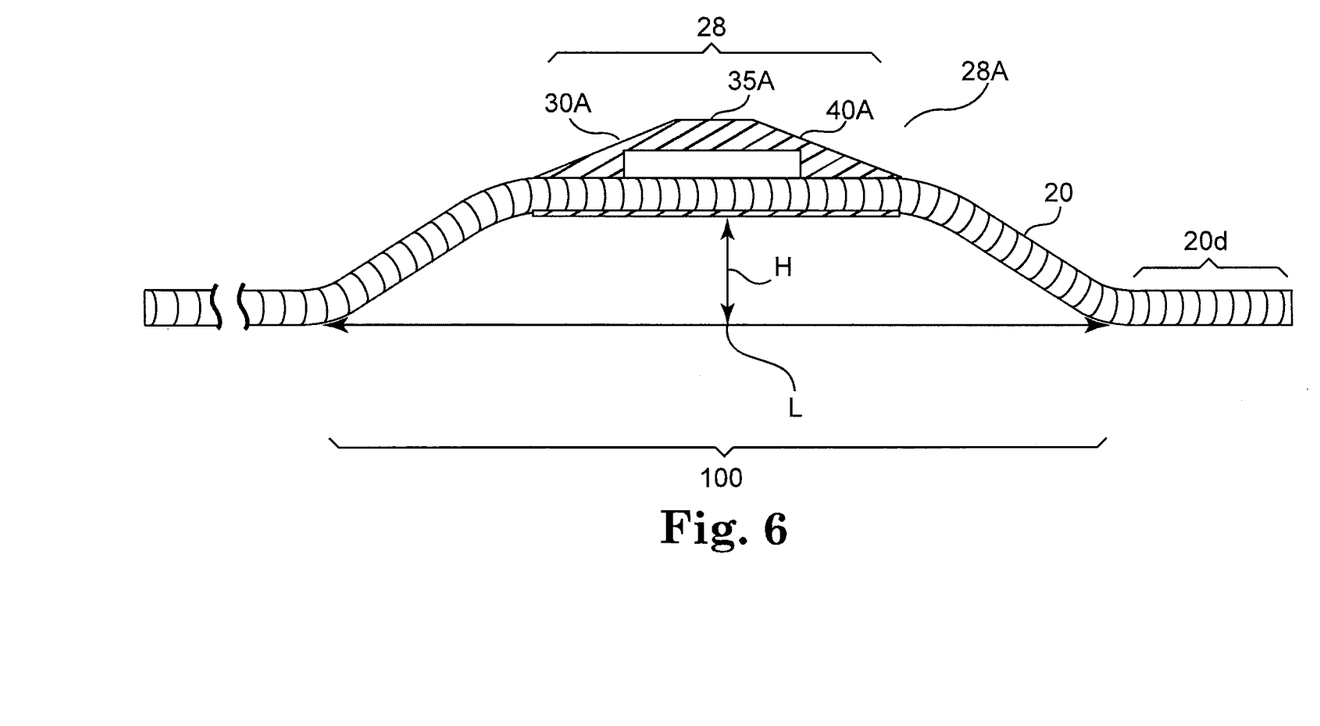
FIG. 6 is a partial cutaway side view of one embodiment of the present invention.

Turning now to FIGS. 6 and 7, one embodiment of the present invention is illustrated with abrasive section 28 comprising an at least partially hollow solid eccentric crown 28A attached to drive shaft 20 as described in connection with FIG. 2 supra. Pre-curved section 100 is provided with height H and length L and formed on the drive shaft 20 proximal to distal portion of drive shaft $20_d$. This illustration of the present invention is without guide wire 15 inserted through the drive shaft lumen (not shown), so that the pre-curved section 100 retains its original pre-curved configuration and profile. FIG. 7 illustrates the deforming straightening of pre-curved section 100 by insertion of guide wire 15 through drive shaft lumen 19 at least through the pre-curved section 100.

Figure 8:
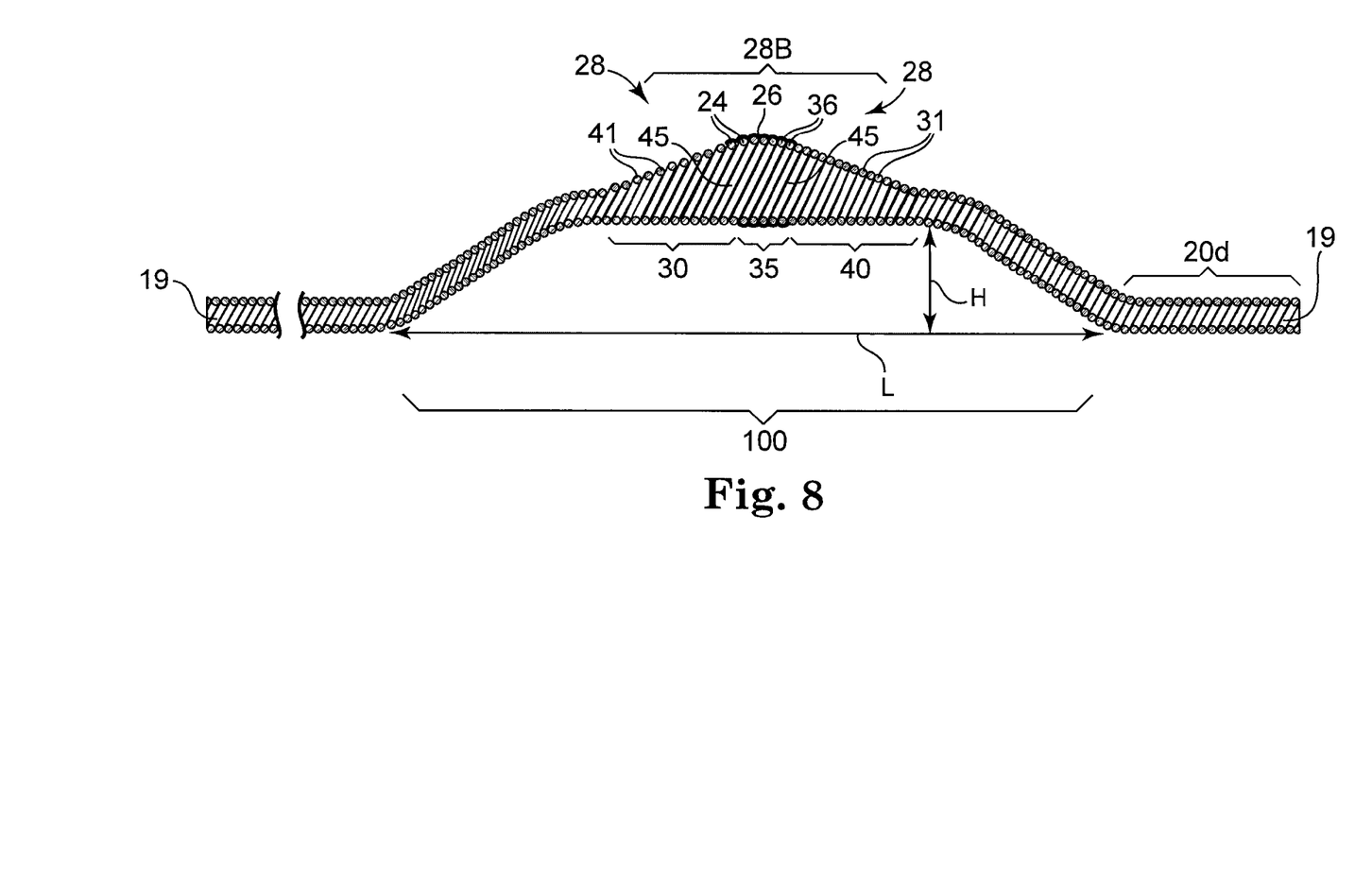
FIG. 8 is a cutaway side view of one embodiment of the present invention.

FIGS. 8 and 9 illustrate another embodiment of the present invention with abrasive section 28 comprising an eccentric enlarged section of drive shaft 28B as described supra in connection with FIG. 3. Thus, pre-curved section 100 is provided with height H and length L and is formed on drive shaft 20 proximal to distal portion of drive shaft $20_d$. FIG. 8 illustrates the pre-curved section 100 in its original curved configuration and profile, without guide wire 15 inserted into drive shaft lumen 19 to straighten pre-curved section 100. FIG. 9 illustrates the deforming straightening effect of guide wire 15 as it is operatively disposed through the lumen 19 of drive shaft 20, in particular through the pre-curved section 100.

The pre-curved section 100 of the present invention thus, comprises a material operating within the material's yield stress and elastic limit and, thus, will have a preformed curved shape that is adaptable to essentially any inner open space of a generally tubular or duct-like lumen to create an orbital pathway that is larger than the resting diameter of the deformed and straightened pre-curved section 100, when the guide wire 15 is disposed through the drive shaft lumen 19 portion corresponding to the pre-curved section 100 as illustrated in, e.g., FIGS. 1, 7 and 9.

The pre-curved section 100 of the drive shaft 20 is thus capable of being elastically (but not plastically) deformed in order to substantially straighten in response to the guide wire 15 being inserted through the drive shaft lumen 19. The pre-curved section of the drive shaft is, therefore, capable of recovering its original curved configuration and profile inside the passageway of the stenosis or lumen when the guide wire is removed from the lumen of the drive shaft, in particular, when the guide wire is drawn proximally away from the pre-curved section 100 of the drive shaft 20.

Significantly and as those skilled in the art will now appreciate, the present invention may allow use of a smaller diameter abrasive section 28, in conjunction with pre-curved section 100, while opening a lumen having a swept diameter equivalent to that of a larger diameter abrasive sections 28 of the prior art that lack pre-curved section 100 of drive shaft 20 as described herein. Alternatively, a larger swept diameter may be realized during high-speed rotation using the pre-bent section 100 of the present invention without increasing the mass of the abrasive section 28 or changing the geometries of the abrasive section 28. In fact, the abrasive section 28 may be made smaller, to further facilitate introduction into torturous vasculature and aid in reduction of trauma using the present invention.

Moreover those skilled in the art will further now recognize any number of combinations and permutations of the above-described parameters for a given rotational speed of the drive shaft 20. Thus, modification of any of these parameters may either increase or decrease/dampen the diameter of the orbital path taken by the abrasive section 28. As such, the diameter of the orbital path may be customized, adapted and/or dynamically adapted for individual lumens and stenoses.

Thus, a method of clearing an stenosis using the present invention may comprise:

providing a guide wire having a maximum diameter less than the diameter of the artery, a flexible elongated, rotatable drive shaft advanceable over the guide wire, and a curvilinear pre-curved section comprising an abrasive section;

deforming the pre-curved section by, e.g., advancing the pre-curved section over the guide wire, to substantially straighten the pre-curved section;

advancing the guide wire and drive shaft into a lumen, e.g., a patient's vasculature to a position proximal the point of interest, e.g., the stenosis to be cleared;

retracting the guide wire proximally;

allowing the pre-curved section to move back into its undeformed and curvilinear profile form;

rotating the drive shaft wherein the pre-curved section and abrasive section sweeps a rotational diameter that is larger than the resting diameter of the drive shaft;

abrading the stenosis;

deforming the pre-curved section by, e.g., reinserting the guide wire, and substantially straightening the pre-curved section in preparation for withdrawal from the lumen, e.g, the patient's vasculature;

withdrawing the guide wire and substantially straightened drive shaft from the lumen.

Alternate embodiments may comprise providing dynamic adaptable control of the curvilinear profile of the pre-curved section by (1) controllably applying current to controllingly heat the pre-curved section comprising, e.g., a shape memory alloy such as Nitinol, to induce curving of the pre-curved section; and/or (2) perfusing a heated biocompatible solution, e.g., saline or ringer's solution, through a catheter advanced over drive shaft and pre-curved section, comprising a shape memory alloy such as Nitinol, to induce curving of pre-curved section.

Figure 10:
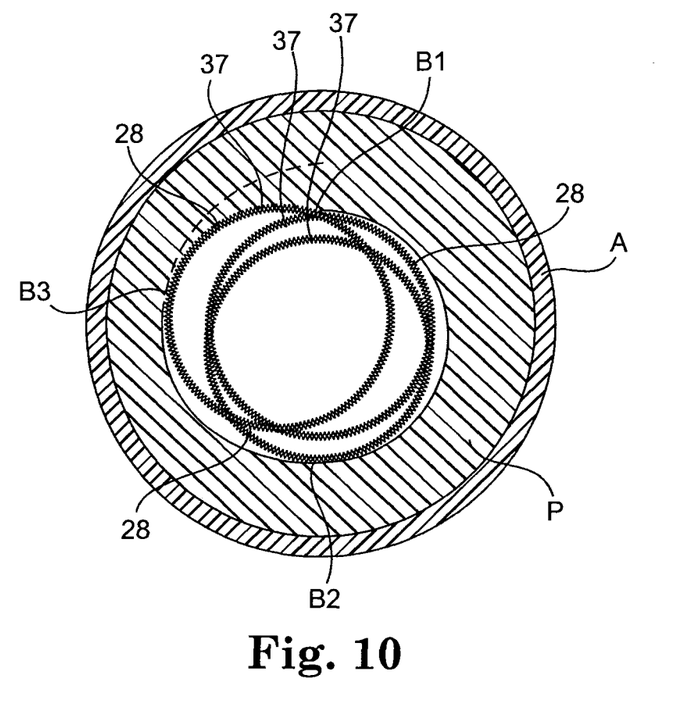
FIG. 10 is a cross-sectional view of one embodiment of the present invention.
Figure 11:
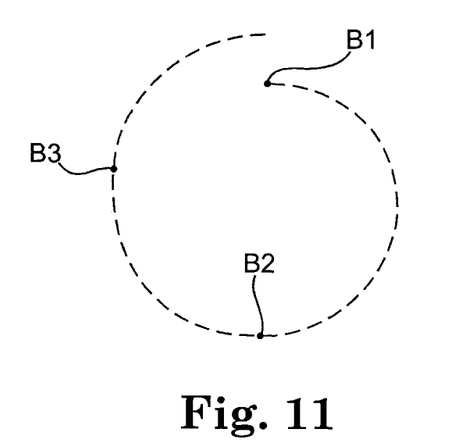
FIG. 11 is a schematic illustrating orbital rotational positions achieved by one embodiment of the present invention.

FIGS. 10 and 11 illustrate the generally spiral orbital path taken by various embodiments of the abrasive section 28 of the present invention, shown without guide wire. The height of the spiral path in FIGS. 10 and 11 is exaggerated for illustrative purposes—in reality, each spiral path of the abrasive section 28 removes only a very thin layer of tissue via the tissue removing surface 37, and many, many such spiral passes are made by the eccentric enlarged abrading head 28 as the device is repeatedly moved forward and backward across the stenosis to fully open the stenosis.

FIG. 11 shows schematically three different rotational positions of the eccentric enlarged abrading head 28 of a rotational atherectomy device of the invention. At each position the abrasive surface of the eccentric enlarged abrading head 28 contacts the stenosis to be removed—the three positions are identified by three different points of contact with the stenosis, those points being designated in the drawing as points B1, B2, and B3. Notice that at each point it is generally the same portion of the abrasive surface of the abrasive section 28 that contacts the tissue—the portion of the tissue removing surface 37 that is radially most distant from the rotational axis of the drive shaft.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A high-speed rotational atherectomy device for opening a stenosis in an artery having a given diameter, comprising:

a guide wire having a maximum diameter less than the diameter of the artery;

a flexible elongated, rotatable drive shaft advanceable over the guide wire the drive shaft comprising a rotational axis and a resting diameter corresponding with a deformed substantially straightened drive shaft, wire turns and a pre-curved section comprising:

a substantially curvilinear profile comprising a single transverse offset of the pre-curved section away from the drive shaft's rotational axis when the drive shaft is not advanced over the guide wire, the single transverse offset having a height and a length, a swept diameter achieved during high-speed rotation of the drive shaft which is larger than the resting diameter, and a deformed and substantially straightened linear profile without the single transverse offset when the drive shaft is advanced over the guide wire; and an eccentric abrading crown attached to the drive shaft at the pre-curved section, the eccentric abrading crown comprising proximal, intermediate and distal portions, wherein the proximal portion comprises a proximal outer surface, the intermediate portion comprises an intermediate outer surface and the distal portion comprises a distal outer surface, the proximal outer surface having diameters that increase distally, the distal outer surface having diameters that decrease distally, and the intermediate outer surface being cylindrical, wherein at least the intermediate outer surface comprise tissue removal sections and wherein the eccentric abrading crown defines a drive shaft lumen therethrough and a hollow cavity, the drive shaft at least partially traversing the drive shaft lumen, the eccentric abrading crown further comprising a center of mass that is radially offset from the rotational axis of the drive shaft when the drive shaft comprises the deformed substantially linear profile.

2. The high-speed rotational atherectomy device of claim 1, wherein the pre-curved section further comprises at least one radiused section.

3. The high-speed rotational atherectomy device of claim 1, wherein the substantially curvilinear profile of the pre-curved section further comprises a proximal radiused section and a distal radiused section.

4. The high-speed rotational atherectomy device of claim 1, wherein the substantially curvilinear profile of the pre-curved section further comprises a peak.

5. The high-speed rotational atherectomy device of claim 4, wherein the eccentric abrading crown is at least partly disposed on the peak.

6. The high-speed rotational atherectomy device of claim 2, wherein the precurved section comprising the substantially curvilinear profile further comprises a peak, the peak comprising at least one point on the drive shaft.

7. The high-speed rotational atherectomy device of claim 6, wherein the precurved section comprising the substantially curvilinear profile comprises a proximal radiused section and a distal radiused section and wherein the peak is substantially linear.

8. The high-speed rotational atherectomy device of claim 3, further comprising the two radiused sections each comprising a curvature, and wherein the curvatures of the proximal radiused section and the distal radiused section are substantially equal.

9. The high-speed rotational atherectomy device of claim 3, further comprising the two radiused sections each comprising a curvature, and wherein the curvatures of the proximal radiused section and the distal radiused section are not substantially equal.

10. The high-speed rotational atherectomy device of claim 1, wherein the drive shaft comprises a distal end and wherein the pre-curved section is disposed proximate the distal end of the drive shaft.

11. The high-speed rotational atherectomy device of claim 1, wherein the drive shaft comprises a rotational axis and wherein the pre-curved section comprises a peak, the peak being transversely offset from the rotational axis of the drive shaft.

12. The high-speed rotational atherectomy device of claim 11, further comprising the eccentric abrading crown being at least partly disposed on the peak of pre-curved section.

13. The high-speed rotational atherectomy device of claim 1, further comprising the pre-curved section being formed of a shape memory alloy.

14. The high-speed rotational atherectomy device of claim 1, further comprising the pre-curved section being formed of a nickel-titanium alloy.

15. The high-speed rotational atherectomy device of claim 1, further comprising the pre-curved section being adapted to a certain curvilinear profile.

16. The high-speed rotational atherectomy device of claim 13, further comprising the pre-curved section being dynamically adaptable to a plurality of curvilinear profiles.

17. A high-speed rotational atherectomy system, comprising:

a guide wire having a maximum diameter less than the diameter of the artery;

a flexible elongated, rotatable drive shaft advanceable over the guide wire, the drive shaft having a rotational axis and a resting diameter corresponding with a deformed substantially straightened drive shaft, and a pre-curved section with an eccentric abrading crown disposed at least partly on the pre-curved section, wherein the pre-curved section comprises a curvilinear profile comprising a single transverse offset of the pre-curved section away from the drive shaft's rotational axis when the pre-curved section is not advanced over the guide wire and the pre-curved section further comprising a deformed and substantially straightened linear profile without the single transverse offset when the pre-curved section is advanced over the guide wire, wherein the pre-curved section comprises a swept diameter achieved during high-speed rotation of the drive shaft which is larger than the resting diameter, the eccentric abrading crown having a lumen, the lumen of the eccentric abrading crown engaging the drive shaft at the pre-curved section, the eccentric abrading crown further comprising a center of mass that is offset from the drive shaft's rotational axis when the drive shaft comprises the deformed and substantially straightened linear profile; and an elongated catheter having a lumen through which at least part of the drive shaft is disposed.

18. The high-speed rotational atherectomy system of claim 17, further comprising:

a fluid supply line operatively connected to the catheter; and a biocompatible solution that is of a controlled temperature, wherein the biocompatible solution is urged through fluid supply line and into the catheter.

19. The high-speed rotational atherectomy system of claim 17, wherein the pre-curved section further comprises a height and a length.

20. The high-speed rotational atherectomy device of claim 17, wherein the pre-curved section further comprises at least one radiused section.

21. The high-speed rotational atherectomy device of claim 17, wherein the pre-curved section further comprises a proximal radiused section and a distal radiused section.

22. The high-speed rotational atherectomy device of claim 17, wherein the curvilinear profile of the pre-curved section further comprises a peak.

23. The high-speed rotational atherectomy device of claim 22, wherein the eccentric abrading crown is at least partly disposed on the peak.

24. The high-speed rotational atherectomy device of claim 17, wherein the curvilinear profile of the pre-curved section further comprises a peak, the peak comprising at least one point on the drive shaft.

25. The high-speed rotational atherectomy device of claim 24, wherein the curvilinear profile of the precurved section comprises two radiused sections and wherein the peak is substantially linear.

26. The high-speed rotational atherectomy device of claim 21, further comprising the proximal and distal radiused sections each comprising a curvature, and wherein the curvatures of the proximal and distal radiused sections are substantially equal.

27. The high-speed rotational atherectomy device of claim 21, further comprising the proximal and distal radiused sections each comprising a curvature, and wherein the curvatures of the proximal and distal radiused sections are not substantially equal.

28. The high-speed rotational atherectomy device of claim 17, wherein the drive shaft comprises a distal end and wherein the pre-curved section is disposed proximate the distal end of the drive shaft.

29. The high-speed rotational atherectomy device of claim 17, wherein the drive shaft comprises a rotational axis and wherein the pre-curved section comprises a peak, the peak being transversely offset from the rotational axis of the drive shaft.

30. The high-speed rotational atherectomy device of claim 29, further comprising the eccentric abrading crown being at least partly disposed on the peak of the pre-curved section.

31. The high-speed rotational atherectomy device of claim 17, further comprising the pre-curved section being formed of a shape memory alloy.

32. The high-speed rotational atherectomy device of claim 17, further comprising the pre-curved section being formed of a nickel-titanium alloy.

33. The high-speed rotational atherectomy device of claim 17, further comprising the pre-curved section being adapted to a certain curvilinear profile.

34. The high-speed rotational atherectomy device of claim 31, further comprising the pre-curved section being dynamically adaptable to a plurality of curvilinear profiles.

* * * * *